United States Patent
Jones et al.

(10) Patent No.: US 7,264,628 B2
(45) Date of Patent: *Sep. 4, 2007

(54) EMBOLIC COIL RETRIEVAL SYSTEM

(75) Inventors: Donald K. Jones, Lauderhill, FL (US); Vladimir Mitelberg, Aventura, FL (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 107 days.

This patent is subject to a terminal disclaimer.

(21) Appl. No.: 11/301,661

(22) Filed: Dec. 13, 2005

(65) Prior Publication Data
US 2006/0135987 A1 Jun. 22, 2006

Related U.S. Application Data

(62) Division of application No. 10/252,615, filed on Sep. 23, 2002, now Pat. No. 6,989,020.

(60) Provisional application No. 60/335,502, filed on Nov. 15, 2001.

(51) Int. Cl.
*A61B 17/28* (2006.01)
(52) U.S. Cl. .................. 606/207; 606/108; 606/200
(58) Field of Classification Search ............. 606/207, 606/205, 200, 108; 623/1.11
See application file for complete search history.

(56) References Cited

U.S. PATENT DOCUMENTS

| | | | |
|---|---|---|---|
| 4,393,872 A * | 7/1983 | Reznik et al. ............ 604/264 |
| 4,997,435 A | 3/1991 | Demeter | |
| 5,053,041 A * | 10/1991 | Ansari et al. ............. 606/148 |
| 5,098,440 A | 3/1992 | Hillstead | |
| 5,217,484 A | 6/1993 | Marks | |
| 5,304,183 A * | 4/1994 | Gourlay et al. ........... 606/142 |
| 5,387,219 A | 2/1995 | Rappe | |
| 5,776,075 A | 7/1998 | Palmer | |
| 5,782,747 A | 7/1998 | Zimmon | |
| 5,840,043 A | 11/1998 | Palmer et al. | |
| 5,868,754 A * | 2/1999 | Levine et al. ............. 606/108 |
| 5,910,144 A | 6/1999 | Hayashi | |
| 6,179,857 B1 | 1/2001 | Diaz et al. | |
| 6,183,491 B1 | 2/2001 | Lulo | |
| 6,241,738 B1 * | 6/2001 | Dereume ................... 606/108 |
| 6,267,783 B1 | 7/2001 | Letendre et al. | |
| 6,270,495 B1 * | 8/2001 | Palermo .................... 606/41 |
| 6,361,558 B1 | 3/2002 | Hieshima et al. | |
| 6,605,111 B2 * | 8/2003 | Bose et al. ............... 623/1.18 |
| 6,673,100 B2 * | 1/2004 | Diaz et al. ............... 623/1.11 |

FOREIGN PATENT DOCUMENTS

DE 298 23 414 U1 6/1999
WO WO95/20914 8/1995

OTHER PUBLICATIONS

European Search Report EP 02 25 7630 dated Mar. 12, 2003.

* cited by examiner

*Primary Examiner*—(Jackie) Tan-Uyen T. Ho
(74) *Attorney, Agent, or Firm*—Michael W. Montgomery

(57) ABSTRACT

An embolic coil retrieval system for retrieving or repositioning an embolic coil within the vasculature of the human body which is comprised of a very small embolic coil retriever having a jaw member with major and minor teeth which form pockets for grasping an embolic coil when the jaw member is closed.

2 Claims, 4 Drawing Sheets

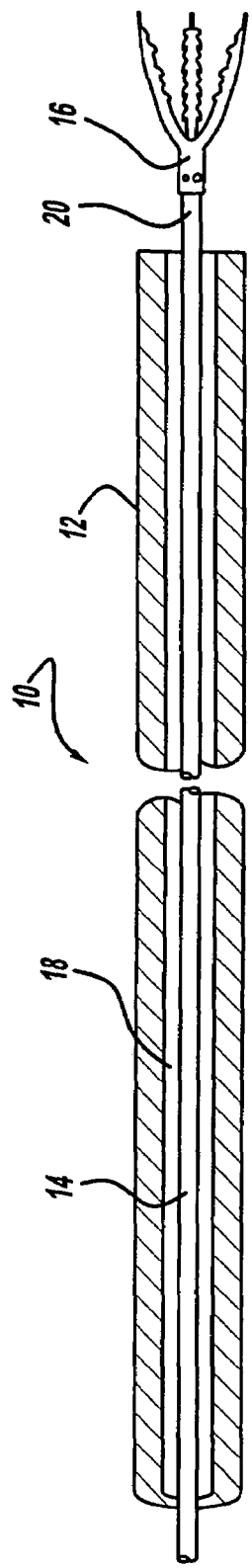
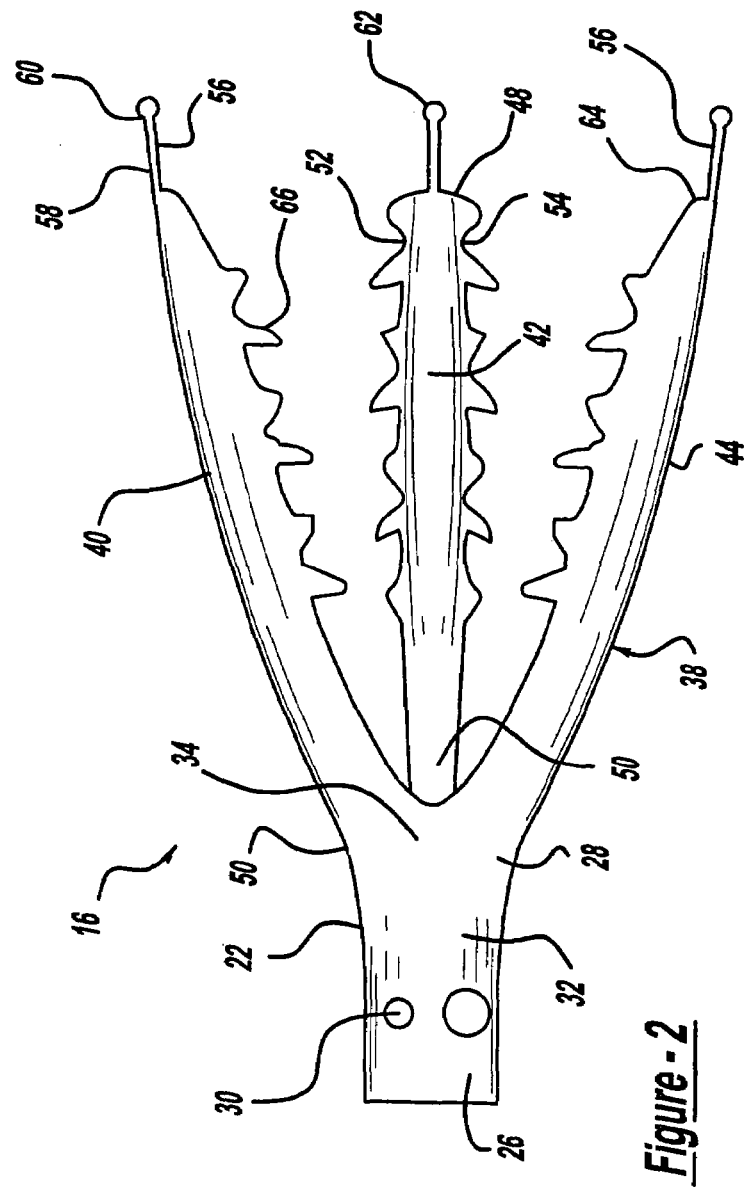
Figure - 1
Figure - 2

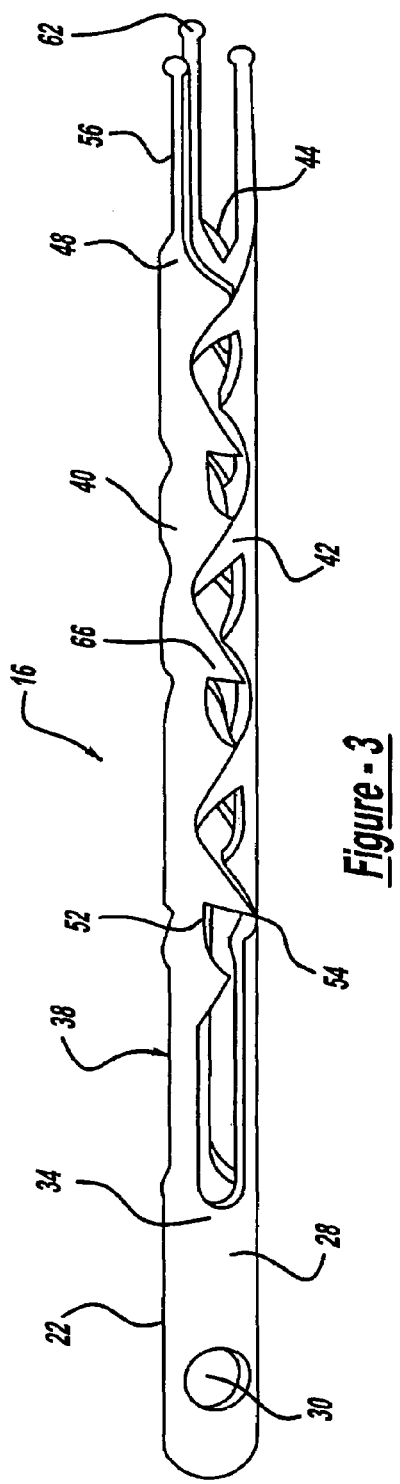
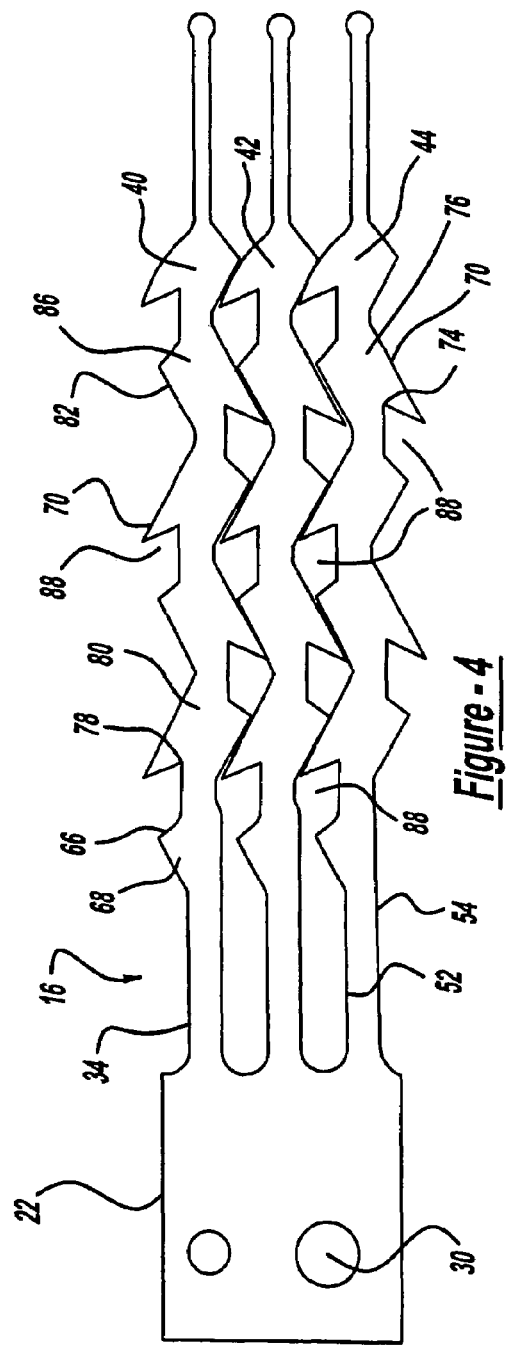

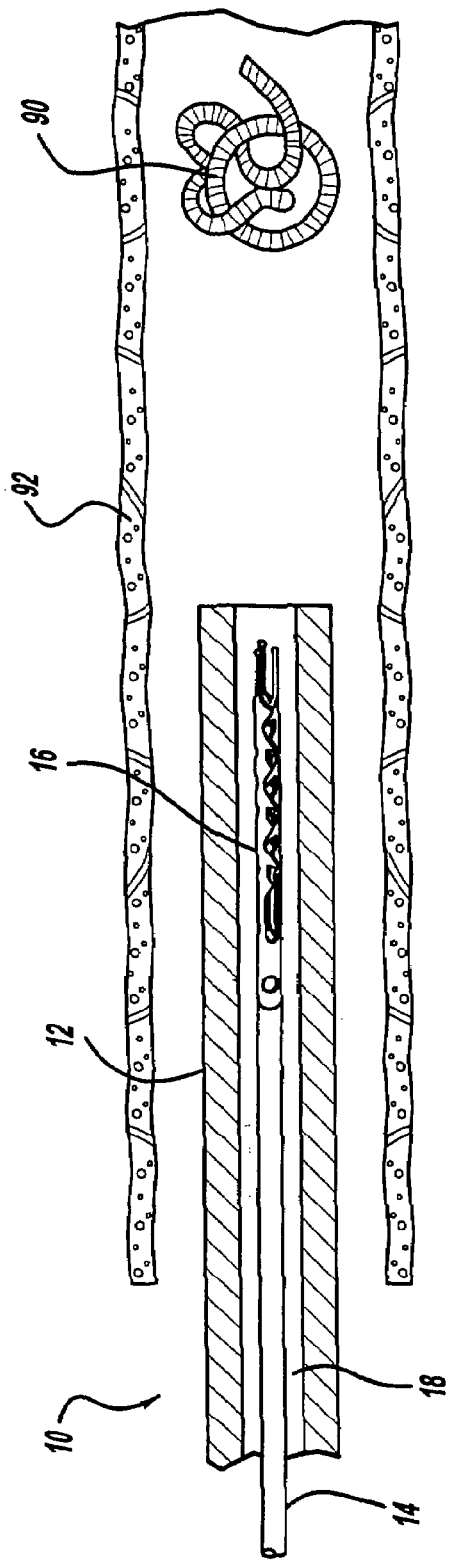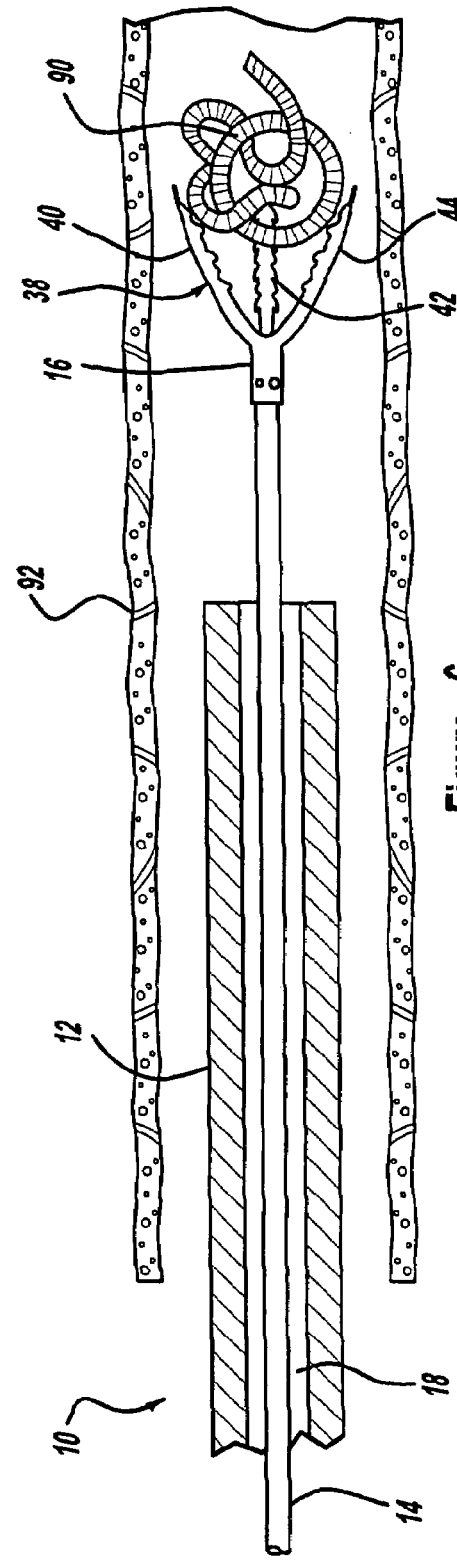

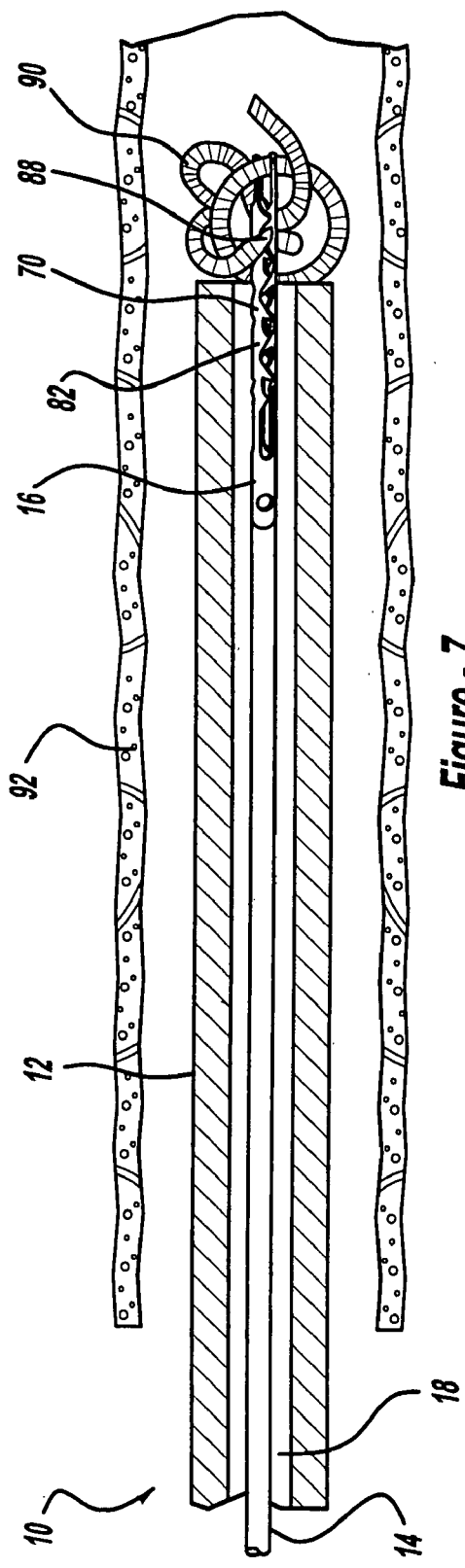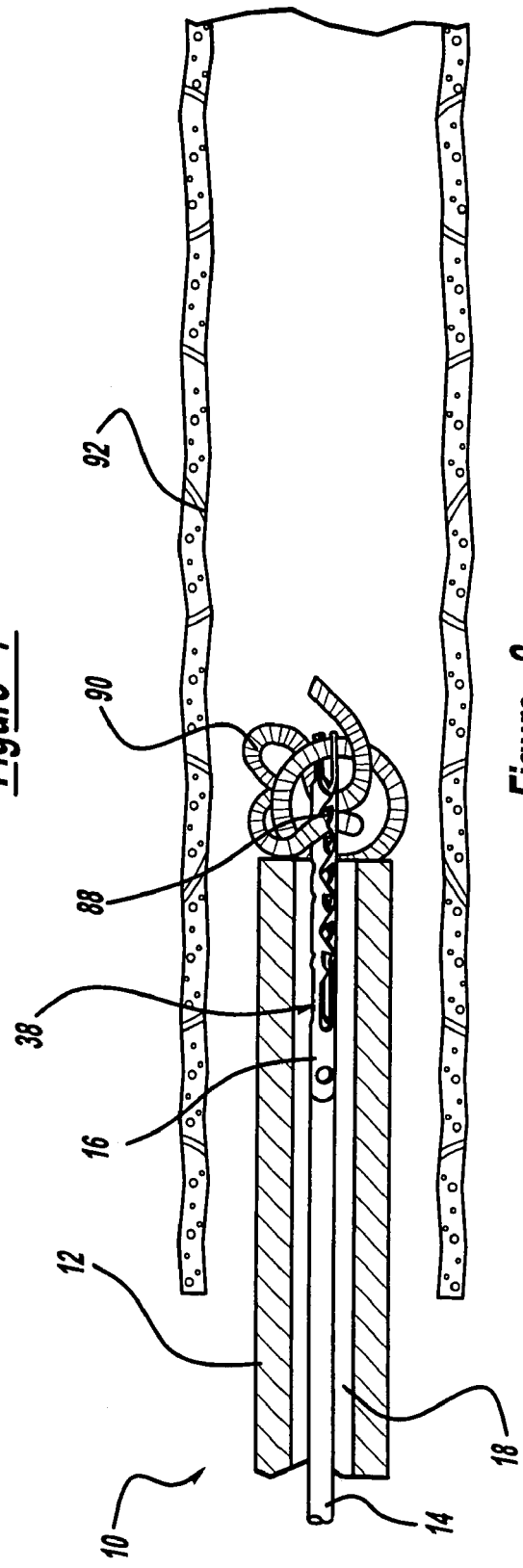

EMBOLIC COIL RETRIEVAL SYSTEM

CROSS-REFERENCE TO RELATED APPLICATION

The patent application is a divisional patent application of U.S. patent application Ser. No. 10/252,615 filed on Sep. 23, 2002, entitled, "Embolic Coil Retrieval System" now U.S. Pat. No. 6,989,020 which is a nonprovisional patent application of U.S. provisional patent application Ser. No. 60/335,502 filed on Nov. 15, 2001, entitled "Three Prong Z-Cut Coil Retriever."

BACKGROUND OF THE INVENTION

1. Field of the Invention

This invention relates to a retrieval system for retrieving of an object within the vasculature of the body, and more particularly to a retrieval system which may be used in the removal of a medical device within a blood vessel. More specifically, the retrieval system may take the form of an embolic coil retrieval system to be used in the removal or repositioning of embolic coils within the brain.

2. Description of the Prior Art

For many years physicians have been placing various devices within a blood vessel of the human body in order to treat an aneurysm or to occlude a vessel by promoting thrombus formation. Such devices include dilatation balloons, liquid medications, stents, and embolic coils. Embolic coils may take the form of helically wound coils, randomly wound coils, coils wound within other coils, or many other coil configurations. These coils are generally formed of radiopaque metallic materials, such as platinum, gold, and tungsten, or alloys of these metals.

U.S. Pat. No. 6,179,857 entitled, "Stretch Resistant Embolic Coil with Variable Stiffness" discloses one such embolic coil design. The coil disclosed in this patent is a helically wound coil in which various combinations of adjacent turns are spot welded together to create a stretch resistant coil of a preselected flexibility. U.S. Pat. No. 6,183,491 entitled, "Embolic Coil Deployment System with Improved Embolic Coil" discloses another coil configuration which shows an embolic coil having a relatively flexible proximal portion which resists stretching.

Instead of placing an embolic coil within an aneurysm to prevent the flow of blood, a stent may be used to treat an aneurysm. U.S. Pat. No. 6,267,783 to Robert P. Letendre, et al discloses one such stent. The stent disclosed in this patent is a self-expanding stent which may be placed within the parent vessel of the aneurysm and positioned over the mouth of the aneurysm to block the flow of blood. Another stent aneurysm treatment device is disclosed in U.S. Pat. No. 6,361,558 entitled, "Stent Aneurysm Treatment System and Method" and assigned to the same assignee as the present application. That patent discloses vasculature stents of various configurations which may also be used as aneurysm covers for occluding, or partially occluding, aneurysms located at various positions along blood vessels.

In certain instances an embolic coil or stent must be removed from the vessel and either repositioned or replaced. Furthermore, a stent may require replacement because it has outlived its useful life. One known procedure for embolic coil or stent removal is surgically removing the device from the vessel. This method however can be time consuming and traumatic to the patient. The development of flexible medical instruments has made it possible to remove embolic coils and stents using minimally invasive surgical procedures.

U.S. Pat. No. 5,098,440 entitled, "Object Retrieval Method and Apparatus" and assigned to the same assignee as the present invention discloses one such device. This patent discloses an apparatus which captures a stent with two criss-cross wire loops. These wire loops slip over a stent, and when the ends of the wires are retracted the loops tighten down on the stent. The stent is captured and withdrawn into a guide catheter.

U.S. Pat. No. 5,217,484 entitled, "Retractable Wire Catheter Device and Method" discloses another apparatus which may be used to retrieve or adjust the position of a deployed vaso-occlusive device. This patent discloses a catheter device having a multi-jaw clamp. When the clamp is placed over a vaso-occlusion wire, a pusher wire is retracted to close the jaws of the clamp thereby capturing the wire for retrieval. A spring jaw medical instrument is disclosed in U.S. Pat. No. 5,782,747 entitled, "Spring Based Multipurpose Medical Instrument." That apparatus, used for capturing an intravascular object, has a variety of jaw structures including a configuration having opposing serrated surfaces for crushing an object and a configuration having a closed loop jaw suitable for grasping an object.

Also, U.S. Pat. No. 5,840,043 entitled, "Jaw Assembly for an Endoscopic Instrument" discloses a retrieval apparatus. This patent describes an instrument which includes a jaw assembly having cups with radially arranged teeth. The jaw assembly with this knife-sharp rim is actuated by a push/pull wire which allows physicians to obtain a multiple sample bioptome.

SUMMARY OF THE INVENTION

There is a need for an improved apparatus and method for retrieving a medical device from the vasculature of the human body. More particularly, there is a need for an apparatus that has a very small diameter and has a jaw assembly which will capture an embolic coil and hold the coil tightly until removed from the vasculature of the body. Such an apparatus could be placed in a very small microcatheter for subsequent positioning within a vessel of the human brain. Obviously, such vessels are extremely small and very tortuous throughout their length.

In accordance with one aspect of the present invention, there is provided an embolic coil retrieval system for capturing an embolic coil in a vessel of the body. The embolic coil retrieval system includes a sheath which takes the form of a flexible elongated tube with a lumen extending therethrough. The sheath has a proximal section and a distal section.

The embolic coil retrieval system also includes an embolic coil retriever having a cylindrical member with a proximal section, a distal section, and a lumen extending therethrough. The embolic coil retriever also has a jaw member including a first jaw, a second jaw, and a third jaw. Each jaw takes the form of a longitudinal portion of an elongated tubular member. Each jaw has a proximal end, a distal end, a first longitudinal edge, and a second longitudinal edge. The proximal ends of the jaws are attached to the distal section of the cylindrical member. Two of the jaws are biased outwardly away from a longitudinal axis of the elongated tubular member. The embolic coil retriever further has a plurality of teeth each having a base. Each tooth generally takes the form of a triangular member. The base of each tooth is attached to the jaw member.

Also, the embolic coil retrieval system includes an actuator wire having a proximal end and a distal end. The wire is slideably disposed within the lumen of the sheath. The distal end of the wire is attached to the proximal section of the cylindrical member.

In accordance with another aspect of the present invention, there is provided an embolic coil retriever for capturing an embolic coil in a vessel of the body. The embolic coil retriever includes a cylindrical member having a proximal section, a distal section, and a lumen extending therethrough. The embolic coil retriever also includes a jaw member having a first jaw, a second jaw, and a third jaw.

Each jaw takes the form of a longitudinal portion of an elongated tubular member. Each jaw has a proximal end, a distal end, a first longitudinal edge, and a second longitudinal edge. The proximal ends of the jaws are attached to the distal section of the cylindrical member. Two of the jaws are biased outwardly away from a longitudinal axis of the elongated tubular member. Finally, the embolic coil retriever includes a plurality of teeth each having a base. Each tooth generally takes the form of a triangular member. The base of each tooth is attached to the jaw member.

In accordance with another aspect of the present invention, there is provided an embolic coil retrieval system for capturing an embolic coil in a vessel of the body. The embolic coil retrieval system includes a sheath which takes the form of a flexible elongated tube with a lumen extending therethrough. The sheath has a proximal section and a distal section.

The embolic coil retrieval system also includes an embolic coil retriever having a cylindrical member with a proximal section, a distal section, and a lumen extending therethrough. The embolic coil retriever also includes a jaw member having a first jaw and a second jaw. Each jaw takes the form of a semicylindrical portion of an elongated tubular member. Each jaw has a proximal end, a distal end, a first longitudinal edge, and a second longitudinal edge. The proximal ends of the jaws are attached to the distal section of the cylindrical member. One of the jaws is biased outwardly away from a longitudinal axis of the elongated tubular member. The embolic coil retriever further includes a plurality of teeth each having a base. Each tooth generally takes the form of a triangular member. The base of each tooth is attached to the jaw member.

Also, the embolic coil retriever system includes an actuator wire having a proximal end and a distal end. The wire is slideably disposed within the lumen of the sheath. The distal end of the wire is attached to the proximal section of the cylindrical member.

In accordance with another aspect of the present invention, there is provided an embolic coil retriever for capturing an embolic coil in a vessel of the body. The embolic coil retriever includes a cylindrical member having a proximal section, a distal section, and a lumen extending therethrough. The embolic coil retriever also includes a jaw member having a first jaw and a second jaw. Each jaw takes the form of a semicylindrical portion of an elongated tubular member.

Each jaw has a proximal end, a distal end, a first longitudinal edge, and a second longitudinal edge. The proximal ends of the jaws are attached to the distal section of the cylindrical member. One of the jaws is biased outwardly away from a longitudinal axis of the elongated tubular member. Finally, the embolic coil retriever includes a plurality of teeth each having a base. Each tooth generally takes the form of a triangular member. The base of each tooth is attached to the jaw member.

In accordance with another aspect of the present invention, there is provided a medical device retrieval system for capturing a medical device in a vessel of the body. The medical device retrieval system includes a sheath which takes the form of a flexible elongated tube with a lumen extending therethrough. The sheath has a proximal section and a distal section.

The medical device retrieval system also includes a medical device retriever including a cylindrical member having a proximal section, a distal section, and a lumen extending therethrough. The medical device retriever also includes a jaw member having a first jaw and a second jaw. Each jaw takes the form of a semicylindrical portion of an elongated tubular member. Each jaw has a proximal end, a distal end, a first longitudinal edge, and a second longitudinal edge. The proximal ends of the jaws are attached to the distal section of the cylindrical member. One of the jaws is biased outwardly away from a longitudinal axis of the elongated tubular member. The medical device retriever further includes a plurality of teeth each having a base. Each tooth generally takes the form of a triangular member. The base of each tooth is attached to the jaw member.

In addition, the medical device retrieval system includes an actuator wire having a proximal end and a distal end. The wire is slideably disposed within the lumen of the sheath. The distal end of the wire is attached to the proximal section of the cylindrical member.

In accordance with still another aspect of the present invention, there is provided a medical device retriever for capturing a medical device in a vessel of the body. The medical device retriever includes a cylindrical member having a proximal section, a distal section, and a lumen extending therethrough. The medical device retriever also includes a jaw member having a first jaw and a second jaw.

Each jaw takes the form of a semicylindrical portion of an elongated tubular member. Each jaw has a proximal end, a distal end, a first longitudinal edge, and a second longitudinal edge. The proximal ends of the jaws are attached to the distal section of the cylindrical member. One of the jaws is biased outwardly away from a longitudinal axis of the elongated tubular member. In addition, the medical device retriever includes a plurality of teeth each having a base. Each tooth generally takes the form of a triangular member. The base of each tooth is attached to the jaw member.

In accordance with another aspect of the present invention, the teeth take the form of major teeth each having an obtuse angle and a base. Each major tooth takes the form of a generally obtuse triangular member. The base of each major tooth has a proximal end and a distal end and is attached to the jaw member. The obtuse angle of each major tooth is located at the proximal end of the base of each major tooth. In addition, the teeth take the form of minor teeth each having a base. Each minor tooth takes the form of a generally acute triangular member. The base of each minor tooth is attached to the jaw member.

In accordance with still another aspect of the present invention, the teeth take the form of minor teeth each having a base and major teeth each having an obtuse angle and a base. Each major tooth takes the form of a generally obtuse triangular member. The base of each major tooth has a proximal end and a distal end and is attached to the jaw member. The obtuse angle of each major tooth is located at the proximal end of the base of the major tooth. Each minor tooth takes the form of a generally acute triangular member. The base of each minor tooth is attached to the jaw member.

In accordance with a similar aspect of the present invention, the first longitudinal edge and second longitudinal edge of each jaw include a pattern of alternating major teeth and minor teeth. Each major tooth is generally aligned with a minor tooth on an adjacent longitudinal edge of an adjacent jaw, and each minor tooth is generally aligned with a major tooth on an adjacent longitudinal edge of an adjacent jaw. The pattern forms a plurality of pockets. The pockets are gaps between the major teeth and minor teeth on the longitudinal edges of the jaws.

In accordance with another aspect of the present invention, the retriever includes a longitudinal leg having a proximal end and a distal end. The proximal end of the longitudinal leg is attached to the distal end of one of the jaws. The longitudinal leg may include a radiopaque marker. In addition, the retriever may include a high density metallic coating and may be formed from a single elongated cylinder.

In accordance with another aspect of the present invention, there is provided an embolic coil retriever for capturing an embolic coil in a vessel of the body. The embolic coil retriever includes a cylindrical member having a proximal section, a distal section, and a lumen extending therethrough. The embolic coil retriever also includes a jaw member having a first jaw and a second jaw.

Each jaw takes the form of a semicylindrical portion of an elongated tubular member. Each jaw has a proximal end, a distal end, a first longitudinal edge, and a second longitudinal edge. The proximal ends of the jaws are attached to the distal section of the cylindrical member. One of the jaws is biased outwardly away from a longitudinal axis of the elongated tubular member. Finally, the embolic coil retriever includes a plurality of teeth attached to said jaw member. Each tooth has a base and a tip. The base of each tooth is attached to the jaw member.

In accordance with a further aspect of the present invention, the teeth take the form of major teeth. Each major tooth has a base and a tip. The base of each major tooth is attached to the jaw member. The tip of each major tooth extends in a direction proximal to the base. In addition, the teeth may take the form of minor teeth. Each minor tooth has a base and a tip. The base of each minor tooth is attached to the jaw member. The tip of each minor tooth extends normal to the base.

In accordance with another aspect of the present invention, the teeth take the form of minor teeth and major teeth. Each major tooth has a base and a tip. The base of each major tooth is attached to the jaw member. The tip of each major tooth extends in a direction proximal to the base. Each minor tooth has a base and a tip. The base of each minor tooth is attached to the jaw member. The tip of each minor tooth extends normal to the base.

In accordance with still another aspect of the present invention, the first longitudinal edge and second longitudinal edge of the first jaw and second jaw include a pattern of alternating major teeth and minor teeth. Each major tooth is generally aligned with a minor tooth on an adjacent longitudinal edge of an adjacent jaw, and each minor tooth is generally aligned with a major tooth on an adjacent longitudinal edge of an adjacent jaw. The pattern forms a plurality of pockets. The pockets are gaps between the major teeth and minor teeth on the longitudinal edges of the jaws.

In accordance with another aspect of the present invention, there is provided a method for capturing an embolic coil or a medical device in a vessel of the body. The method includes the step of providing an embolic coil retrieval system or medical device retrieval system including a sheath, an embolic coil retriever or medical device retriever having a cylindrical member, a jaw member including a first jaw, a second jaw, and a third attached to the cylindrical member, a plurality of teeth attached to the jaw member, and an actuator wire attached to the cylindrical member.

The method also includes the step of inserting the embolic coil retrieval system or medical device retrieval system into the vasculature of the human body then pushing the actuator wire distally through the sheath causing the embolic coil retriever or medical device retriever to exit a distal end of the sheath thereby allowing the jaws of the embolic coil retriever or medical device retriever to open. The method further includes moving the embolic coil retriever or medical device retriever distally to align the jaws with an embolic coil or medical device then pushing the sheath distally causing the jaws to close around the embolic coil or medical device. In addition, the method includes the step of removing the embolic coil retrieval system or medical device retrieval system from the vasculature of the body.

These and other aspects of the invention and the advantages thereof will be clearly understood from the following description and drawings of a preferred embodiment of the present invention.

BRIEF DESCRIPTION OF THE DRAWINGS

FIG. 1 is an enlarged, sectional view of an embolic coil retrieval system including a sheath, an actuator wire, and an embolic coil retriever;

FIG. 2 is an enlarged, perspective view of an embolic coil retriever with a jaw member in an open position;

FIG. 3 is an enlarged, perspective view of an embolic coil retriever with the jaw member in a closed position;

FIG. 4 is a side elevational view of the embolic coil retriever illustrated in FIG. 3 with the embolic coil retriever being cut along a longitudinal line and flattened into a single plane;

FIG. 5 is an enlarged, sectional view of the embolic coil retrieval system being inserted into a vessel;

FIG. 6 is an enlarged, sectional view showing the actuator wire being moved distally causing the jaw member of the embolic coil retriever to exit the lumen of the sheath and to assume the open position;

FIG. 7 is an enlarged, sectional view showing the sheath being moved distally causing the jaw member of the embolic coil retriever to re-enter the lumen of the sheath and to assume the closed position around the embolic coil; and, FIG. 8 is an enlarged, sectional view showing the embolic coil retrieval system and the embolic coil being removed from the vessel.

DESCRIPTION OF THE PREFERRED EMBODIMENT

FIG. 1 illustrates an embolic coil retrieval system 10 which includes a sheath 12, an actuator wire 14, and an embolic coil retriever 16. The sheath 12 is approximately 60 inches in length and is preferably formed of a polymer material with a durometer in the range of about 50 D and 80 D. The outside diameter of the sheath 12 is about 0.038 inches while the lumen 18 of the sheath 12 has a diameter of approximately 0.021 inches. The actuator wire 14 is approximately 70 inches in length and is preferably made from a metallic material. The diameter of the actuator wire 14 is less than the diameter of the lumen 18 of the sheath 12 so that the actuator wire 14 may slide within the lumen 18 of the sheath 12. The embolic coil retriever 16 is laser cut from a nickel-titanium alloy tube and is attached to the distal end 20 of the actuator wire 14.

FIG. 2 illustrates the embolic coil retriever 16 in a normally open configuration. The embolic coil retriever 16 includes a cylindrical member 22 with a lumen 24 (not shown), a proximal section 26, and distal section 28. The cylindrical member 22 is approximately 0.040 inches in length and is preferably formed from a nickel-titanium alloy. The outside diameter of the cylindrical member 22 is about 0.018 inches while the diameter of the lumen 24 is approximately 0.012 inches. There are attachment holes 30 in the wall 32 of the cylindrical member 22 which allow the distal end 20 of the actuator wire 14 to be attached within the lumen 24 of the cylindrical member 22.

Attached to the distal section 28 of the cylindrical member 22 is an elongated tubular member 34 which is approximately 0.12 inches in length and is also preferably made from a nickel-titanium alloy. The outside diameter of the elongated tubular member 34 and the diameter of the lumen 36 (not shown) of the tubular member 34 are generally the same as the cylindrical member 22. A jaw member 38 is formed from the elongated tubular member 24. Preferably, the jaw member 38 is laser cut from the elongated tubular member 34. The jaw member 38 includes a first jaw 40, a second jaw 42, and a third jaw 44 where each jaw 40, 42, and 44 takes the form of a longitudinal portion of the elongated tubular member 34. Each jaw 40, 42, and 44 has a distal end 48, a proximal end 50, a first longitudinal edge 52, and a second longitudinal edge 54. The distal ends 48 of the jaws 40, 42, and 44 are biased outwardly such that the distal ends 48 are approximately 0.008 inches from the longitudinal axis of the elongated tubular member 34.

The first jaw 40, second jaw 42, and third jaw 44 include longitudinal legs 56 having a proximal end 58 and a distal end 60. The proximal ends 58 of the longitudinal legs 56 are attached to the distal ends 48 of the jaws 40, 42, and 44. The longitudinal legs 56 are approximately 0.002 inches in length and may include a radiopaque marker 62 for use during fluoroscopic visualization. Preferably, the longitudinal legs 56 are laser cut from the elongated tubular member 34. Attached to the first longitudinal edges 52 and second longitudinal edges 54 of the jaws 40, 42, and 44 are teeth 66. These teeth 66 are described in more detail in the description of FIG. 4.

FIG. 3 illustrates the embolic coil retriever 16 in a closed configuration. The overall length of the embolic coil retriever 16 in the closed position is approximately 0.16 inches. The cylindrical member 22 includes attachment holes 30 (one shown) for the actuator wire 14. The elongated tubular member 34 which takes the form of a jaw member 38 is attached to the distal section 28 of the cylindrical member 22. The jaw member 38 includes a first jaw 40, a second jaw 42, and a third jaw 44. As can be appreciated, each jaw 40, 42, and 44 takes the form of a longitudinal portion of the elongated tubular member 34. At the distal ends 48 of the jaws 40, 42, and 44, longitudinal legs 56 are attached which may include radiopaque markers 62. Each jaw 40, 42, and 44 of the jaw member 38 includes teeth 66 attached to the first longitudinal edge 52 and second longitudinal edge 54. This configuration of the teeth 66 is described below.

FIG. 4 illustrates the teeth 66 of the embolic coil retriever 16. The teeth 66 generally take the form of triangular members each having a base 68 attached to a longitudinal edge 52 and 54 of a jaw 40, 42, and 44. Preferably, the teeth 66 are laser cut from the elongated tubular member 34. The teeth 66 may take the form of major teeth 70 which are generally obtuse triangular members having an obtuse angle 74 and a base 76. The base 76 of each major tooth 70 has a proximal end 78 and a distal end 80. The obtuse angle 74 of each major tooth 70 is located at the proximal end 78 of the base 76. The teeth 66 may also take the form of minor teeth 82 which are generally acute triangular members having a base 86. The base 86 of each minor tooth 82 is attached to a longitudinal edge 52 and 54 of a jaw 40, 42, and 44.

The configuration of the teeth 66 shown in FIG. 4 includes a combination of major teeth 70 and minor teeth 82. There is a pattern of alternating major teeth 70 and minor teeth 82 along the longitudinal edges 52 and 54 of each jaw 40, 42, and 44. In addition, each major tooth 70 is generally aligned with a minor tooth 82 on an adjacent longitudinal edge 52 and 54 of an adjacent jaw 40, 42, and 44, and each minor tooth 82 is generally aligned with a major tooth 70 on an adjacent longitudinal edge 52 and 54 of an adjacent jaw 40, 42, and 44. This pattern forms a plurality of pockets 88 which are gaps between the major teeth 70 and the minor teeth 82 on the longitudinal edges 52 and 54 of the jaws 40, 42, and 44. Each pocket 88 is approximately 0.015 inches wide and 0.015 inches tall. However, the size of the pocket 88 may be varied so as to generally match the size of the pockets 88 with the size of the embolic coil 90 being retrieved.

FIGS. 5 through 8 illustrate a preferred method of using the embolic coil retrieval system 10 to capture an embolic coil 90. In FIG. 5, the embolic coil retrieval system 10 is inserted into the vasculature 92 of the human body. The embolic coil retriever 16 is attached to the actuator wire 14 and is disposed within the lumen 18 of the sheath 12. The embolic coil retrieval system 10 is moved distally towards the embolic coil 90 to be retrieved. FIG. 6 shows the actuator wire 14 being moved distally causing the embolic coil retriever 16 to exit the lumen 18 of the sheath 12 thereby causing the jaws 40, 42, and 44 of the jaw member 38 of the embolic coil retriever 16 to assume a normally open position. The jaw member 38 in the open position is aligned with the embolic coil 90 to be retrieved.

In FIG. 7, the sheath 12 is moved distally causing the jaws 40, 42, and 44 of the embolic coil retriever 16 to assume a closed position around the embolic coil 90. The embolic coil 90 is captured within the pockets 88 formed by the gaps between the alternating major teeth 70 and minor teeth 82 on the jaws 40, 42, and 44. FIG. 8 illustrates the embolic coil retrieval system 10 and the embolic coil 90 being removed from the vasculature of the body. As the embolic coil retrieval system 10 is moved proximally, the embolic coil 90 is held within the pockets 88 and is wedged behind major teeth 70 thereby preventing the embolic coil 90 from falling out of the jaw member 38.

A novel system has been disclosed in which an embolic coil retrieval system is introduced into the vasculature of the human body for retrieval of an embolic coil. Although a preferred embodiment of the invention has been described, it is to be understood that various modifications may be made by those skilled in the art without departing from the scope of the present invention.

For example, there may be variations to the jaw member of the embolic coil retriever. The jaw member may include four or more jaws formed from an elongated tubular member. Each jaw may be a longitudinal portion of the elongated tubular member. In another alternative construction, the embolic coil retriever may be covered with a high density metallic coating, like gold. This coating may provide enhanced reflection during fluoroscopic visualization.

In still another alternative construction, the pockets formed by the major teeth and minor teeth along the longitudinal edges of the jaws may vary in size. For example, at the distal end of the jaw member the pockets may be small for capturing small embolic coils, but pockets may gradually become larger towards the proximal end of the jaw member for capturing larger embolic coils. This construction would allow physicians to use one jaw member configuration for capturing various sized embolic coils.

Finally, the embolic coil retriever may be used for capturing other medical devices such as dilation balloons or stents.

These and other modifications would be apparent to those having ordinary skill in the art to which this invention relates and are intended to be within the scope of the claims which follow.

That which is claimed is:

1. A method for capturing an embolic coil in a vessel of the body, said method comprising the steps of:

providing an embolic coil retrieval system comprising a sheath and an embolic coil retriever comprising a cylindrical member, a jaw member including a first jaw with a first longitudinal edge, a second jaw with a second longitudinal edge, and a third jaw with a third longitudinal edge, wherein the first, second and third jaws are attached to said cylindrical member, a plurality of teeth attached to said jaw member, and an actuator wire attached to said cylindrical member, and wherein said longitudinal edges of said first jaw, said second jaw, and said third jaw comprise a pattern of alternating major teeth and minor teeth, the major and minor teeth of one jaw cooperating with the major and teeth of an adjacent jaw to define a plurality of gaps between said major teeth and said minor teeth on said longitudinal edges of said jaws when the jaws are in a closed position;

inserting said embolic coil retrieval system into the vasculature of the human body;

pushing said actuator wire distally through said sheath causing said embolic coil retriever to exit a distal end of said sheath thereby allowing said jaws of said embolic coil retriever to open;

moving said embolic coil retriever distally to align said jaws of said embolic coil retriever with an embolic coil;

pushing said sheath distally causing said jaws of said embolic coil retriever to close around said embolic coil; and, removing said embolic coil retrieval system from a vessel of the body.

2. A method for capturing a medical device in a vessel of the body, said method comprising the steps of:

providing a medical device retrieval system comprising a sheath, a medical device retriever comprising a cylindrical member, a jaw member including a first jaw with a first longitudinal edge, a second jaw with a second longitudinal edge, and a third jaw with a third longitudinal edge, wherein the first, second and third jaws are attached to said cylindrical member, a plurality of teeth attached to said jaw member, and an actuator wire attached to said cylindrical member, and wherein said longitudinal edges of said first jaw, said second jaw, and said third jaw comprise a pattern of alternating major teeth and minor teeth, the major and minor teeth of one jaw cooperating with the major and teeth of an adjacent jaw to define a plurality of gaps between said major teeth and said minor teeth on said longitudinal edges of said jaws when the jaws are in a closed position;

inserting said medical device retrieval system into the vasculature of the human body;

pushing said actuator wire distally through said sheath causing said medical device retriever to exit a distal end of said sheath thereby allowing said jaws of said medical device retriever to open;

moving said medical device retriever distally to align said jaws of said medical device retriever with a medical device;

pushing said sheath distally causing said jaws of said medical device retriever to close around said medical device; and, removing said medical device retrieval system from a vessel of the body.

* * * * *